United States Patent
Jen et al.

(10) Patent No.: US 12,383,288 B2
(45) Date of Patent: Aug. 12, 2025

(54) SELF-ACTUATING GRASPING DEVICE

(71) Applicant: Prodeon Medical Corporation, Taipei (TW)

(72) Inventors: Jimmy Jen, Saratoga, CA (US); Kenneth Chih-Ping Chang, San Jose, CA (US); Craig Purdy, Sunnyvale, CA (US); Gary Daniel Zaretzka, Sunnyvale, CA (US); Po-Hua Lee, Sunnyvale, CA (US)

(73) Assignee: Prodeon Medical Corporation, Taipei (TW)

( * ) Notice: Subject to any disclaimer, the term of this patent is extended or adjusted under 35 U.S.C. 154(b) by 117 days.

(21) Appl. No.: 17/367,704

(22) Filed: Jul. 6, 2021

(65) Prior Publication Data

US 2022/0008093 A1    Jan. 13, 2022

Related U.S. Application Data (60) Provisional application No. 63/048,289, filed on Jul. 6, 2020.

(51) Int. Cl.
  *A61B 17/22* (2006.01)
  *A61B 17/29* (2006.01)

(52) U.S. Cl.
  CPC ......... *A61B 17/22031* (2013.01); *A61B 2017/22034* (2013.01); *A61B 2017/22035* (2013.01); *A61B 17/29* (2013.01); *A61B 17/2909* (2013.01)

(58) Field of Classification Search
  CPC .......... A61B 17/29; A61B 17/2909; A61B 2017/2912; A61B 2017/2919;
  (Continued)

(56) References Cited

U.S. PATENT DOCUMENTS

| 4,258,716 A | 3/1981 | Sutherland |
|---|---|---|
| 4,763,668 A | 8/1988 | Macek et al. |

(Continued)

FOREIGN PATENT DOCUMENTS

| JP | H09038097 A | 2/1997 |
|---|---|---|
| JP | 2009195351 A | 9/2009 |
| WO | 199408514 A1 | 4/1994 |

OTHER PUBLICATIONS

International Search Report and Written Opinion from corresponding International Patent Application No. PCT/US2021/040435, dated Oct. 25, 2021.

(Continued)

*Primary Examiner* — Dianne Dornbusch
(74) *Attorney, Agent, or Firm* — Dergosits & Noah LLP; Todd A. Noah (57) ABSTRACT

An self-actuating grasping device and corresponding method of using the grasping device for retrieving a foreign object from a location in a patient's body. The grasping device has a handle with a self-actuating mechanism, an actuator on the handle coupled to an actuator wire, an elongated shaft member extending distally from the handle with the actuation wire coaxially disposed therein and opposing jaws at a distal end of the elongated shaft member that are coupled to the actuation wire and pivot between open and closed configurations. The self-actuating mechanism has a bias that imparts a closing force to the opposing jaws through the actuation wire. Actuation of the actuator is configured to impart an opening force to the opposing jaws through the actuation wire.

21 Claims, 7 Drawing Sheets

(58) Field of Classification Search
CPC .............. A61B 2017/292; A61B 1/307; A61B 1/00128; A61B 17/22031; A61B 2017/22034; A61B 2017/22035; A61M 25/0097

See application file for complete search history.

(56) References Cited

U.S. PATENT DOCUMENTS

| | | | |
|---|---|---|---|
| 4,865,030 A | 9/1989 | Polyak | |
| 5,304,203 A * | 4/1994 | El-Mallawany | A61B 17/29 606/205 |
| 5,578,056 A | 11/1996 | Pauldrach | |
| 5,601,578 A * | 2/1997 | Murphy | A61B 17/0469 606/139 |
| 5,807,378 A * | 9/1998 | Jensen | B25J 15/04 606/1 |
| 5,827,323 A * | 10/1998 | Klieman | A61B 17/2909 606/205 |
| 2001/0049540 A1 | 12/2001 | Santilli | |
| 2007/0186933 A1 | 8/2007 | Domingo et al. | |
| 2009/0131932 A1 * | 5/2009 | Vakharia | A61L 2/206 606/45 |
| 2011/0301600 A1 * | 12/2011 | Garrison | A61B 18/1206 606/49 |
| 2012/0016346 A1 * | 1/2012 | Steinmetz | A61M 25/01 604/535 |

OTHER PUBLICATIONS

International Preliminary Report on Patentability from corresponding International Patent Application No. PCT/US2021/040435, dated Jan. 10, 2023.
Anonymous: "Extract From the Pediatric Surgery Catalog Urology," Storz the World of Endoscopy, Jan. 1, 2019, pp. 1-40, XP055914903.
Extended European Search Report from corresponding European Patent Application No. 21838443.6 dated Jun. 3, 2024.
Office Action from corresponding Japanese Patent Application No. 2023-500362 dated Dec. 24, 2024.

* cited by examiner

SELF-ACTUATING GRASPING DEVICE

RELATED APPLICATIONS

This application claims priority to U.S. Provisional Application No. 63/048,289, filed Jul. 6, 2020. The priority of this application is expressly claimed, and the disclosure is hereby incorporated by reference in its entirety.

FIELD OF THE PRESENT DISCLOSURE

This disclosure relates to devices for managing or treating body tissues obstructing a hollow body lumen, such as the prostatic lobe tissues obstructing the urethra.

BACKGROUND

The prostate is a walnut-shaped gland that wraps around the urethra through which urine is expelled from the bladder and plays a crucial role in the reproductive system of men. Although the gland starts out small, it tends to enlarge as a man ages. An excessively enlarged prostate results in a disease known as benign prostatic hyperplasia (BPH). Benign prostatic hyperplasia (BPH) refers to the abnormal, but non-malignant (non-cancerous) growth of the prostate observed very commonly in aging men. BPH is a chronic condition and is associated with the development of urinary outflow obstruction or luminal narrowing of the prostatic urethra. Bladder outlet obstruction (BOO) refers to a blockage at the base of the bladder that reduces or stops the flow of urine into the urethra and may be secondary to BPH. A range of related disorders referred to collectively as Lower Urinary Tract Symptoms (LUTS) can result, including voiding or obstructive symptoms such as hesitancy, poor and/or intermittent stream, straining, prolonged micturition, feeling of incomplete bladder emptying, dribbling, etc, and storage or irritative symptoms such as frequency, urgency, urge incontinence, and nocturia. These symptoms can also cause sexual dysfunction, urinary retention, urinary leakage, and urinary tract and bladder infections which can worsen as the abnormal growth in the prostate progresses.

Although traditional surgical intervention can be performed, less invasive techniques include implanting a device within the prostatic urethra that is designed to increase the diameter of the urethra. Placing a prostatic implant involves a procedure wherein the urologist inserts a small device within the prostatic urethra which is narrowed by enlarged prostatic tissue. Once in place, the implant is designed to expand and help keep the urethra open by pushing out the tissue lobes, while preventing enlarged prostate tissue from total impingement and opening of the urethra. Ideally, prostatic implants eliminate the need to surgically remove prostatic tissue and are expected to reduce the risks of hematuria, catheterization, sexual dysfunction, and incontinence, inherent and traditional to even less-invasive, surgical approaches. The procedure may also be designed to be reversible since the implants may be removed and additional surgical treatments may be performed in the future. Removal of a prostatic implant, such as a stent or a prostatic tissue expander, is typically accomplished using a grasper that can be inserted through the working lumen of a cystoscope in conjunction with a sheath as described in co-pending, commonly owned U.S. application Ser. No. 17/109,814, filed Dec. 2, 2020, which is hereby incorporated by reference in its entirety. The cystoscope is inserted through a sheath and both are inserted into the urethra, as a system, under direct imaging using the cystoscope. The user secures the implant using the grasper and pulls it into the sheath. In other contexts, a grasper can be used to retrieve other types of foreign bodies from the urinary tract, including those responsible for blockages or obstructions, such as stones or calculi, in the urethra, urinary bladder, ureters and kidneys. Moreover, it should also be appreciated that a grasper can be used in minimally invasive procedures to remove such foreign bodies from other parts of the body, including without limitation the pancreas, esophagus, gallbladder, kidneys and others.

Figure 1:
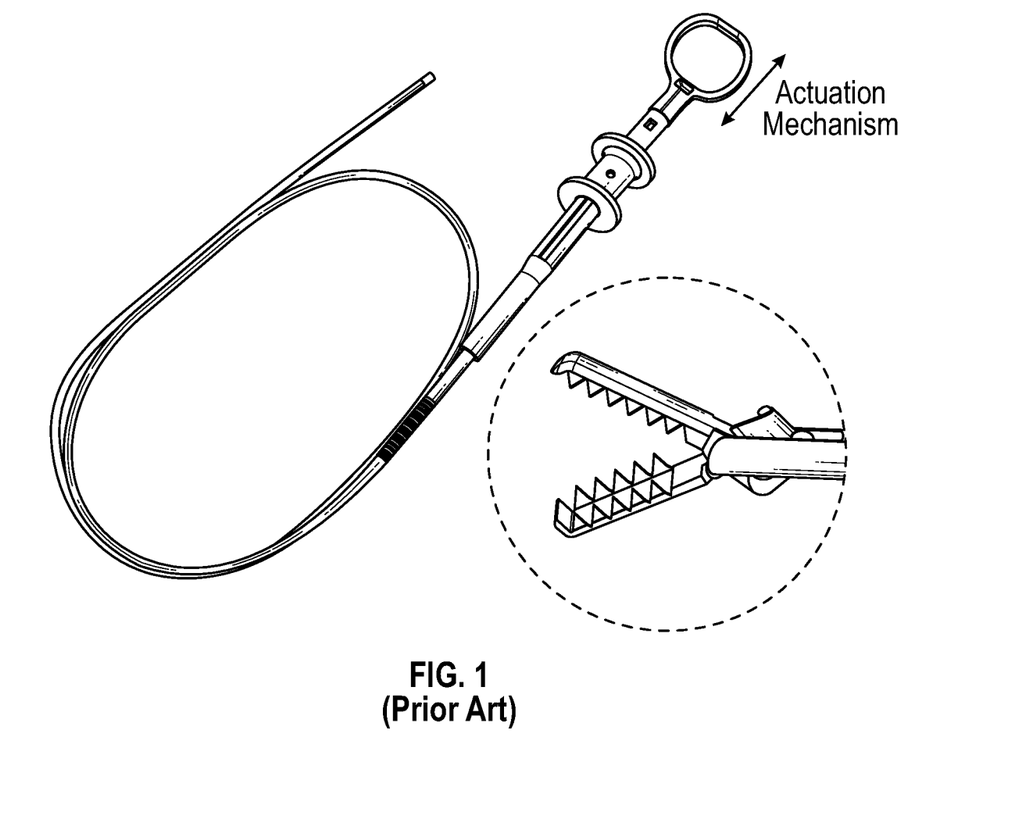
FIG. 1 is an example of a prior art grasper.

For embodiments of graspers configured for use during urology procedures to remove a stent or a tissue expander, the grasper is flexible, with an outer diameter of between approximately 2-3 mm or less depending on the required compatibility with specific flexible or rigid cystoscopes. These characteristics can be adapted as warranted for other procedures or to access other parts of the body. Conventionally available graspers rely on a push and pull handle actuation mechanism, such as the prior art example shown in FIG. 1. To actuate the distal jaw and grasp a foreign object, the user has to pull on the thumb handle to open the distal jaw and push to close the jaw. Typically, the grasper jaws are free and may be in the open or closed position. If the user wants to continuously hold the jaw in the closed position, i.e., after securing the tissue expander or any foreign object, the user must apply a constant forward pressure to the handle which is not desirable for the user. For example, this requirement can increase hand fatigue and/or limit operator capabilities during the clinical procedures, leading to undesirable consequences. Sometimes, an assistant or a second user will be required to operate the grasper and hold it in the closed position to minimize fatigue. The need for two operators during the clinical procedure in turn requires coordinated action to grasp and retrieve the foreign object and lengthen the procedure, as well as require increased usage of resources. Correspondingly, it would be beneficial to provide a self-actuating grasper that stays locked after grasping the foreign object that reduces hand fatigue, and enables a single operator to retrieve a foreign object from the urinary tract, urinary system or other parts of the body. The techniques of this disclosure satisfy these and other needs.

SUMMARY

This disclosure is directed to a grasping device having a handle with a self-actuating mechanism, an actuator on the handle coupled to an actuator wire, an elongated shaft member extending distally from the handle with the actuation wire coaxially disposed therein and opposing jaws at a distal end of the elongated shaft member that are coupled to the actuation wire and pivot between an open configuration and a closed configuration. The self-actuating mechanism has a bias that imparts a closing force to the opposing jaws through the actuation wire and actuation of the actuator is configured to impart an opening force to the opposing jaws through the actuation wire.

In one aspect, the self-actuating mechanism may be a plunger coupled to the actuation wire and disposed within a barrel of the handle, wherein the plunger is biased to apply the closing force by a spring. The spring may be a compression spring such that the plunger is biased in a proximal direction and the closing force is a withdrawal force applied to the actuation wire. The actuator may be configured to impart the opening force in a distal direction when the user applies a distal force to the actuator. Alternatively, the actuator may be configured to impart the opening force in a distal direction when the user applies a withdrawal force to the actuator.

In one aspect, an extension of the actuator may be coupled to the plunger by a rotating link that reverses the direction of force applied through the actuator.

In one aspect, the actuator may be configured to augment the closing force when force is applied to the actuator in a direction opposite of that associated with the opening force.

In one aspect, the spring is an extension spring such that the plunger is biased in a distal direction and the closing force is a distal force applied to the actuation wire. The actuator may be configured to impart the opening force in a withdrawal direction.

In one aspect, the grasping device also has an adapter configured to provide direct connection to a cystoscope or other imaging equipment or devices used in medical procedures. The adapter may have a barrel extension telescopically disposed within a body allowing a position of the grasping device relative to the cystoscope to be adjusted, to accommodate different cystoscope lengths or fix the position of the grasper relative to the foreign object and the cystoscope. The barrel extension may be configured to be locked in an adjusted position. The adapter may also have an irrigation port.

This disclosure also includes a method for retrieving a foreign object from a location in a patient's body. The method may involve providing a grasping device having a handle with a self-actuating mechanism, an actuator on the handle coupled to an actuator wire, an elongated shaft member extending distally from the handle with the actuation wire coaxially disposed therein and opposing jaws at a distal end of the elongated shaft member that are coupled to the actuation wire and pivot between an open configuration and a closed configuration. The grasping device may be advanced through a lumen of a medical device until the opposing jaws are adjacent to the foreign object. An opening force may be applied through the actuation wire to the opposing jaws with the actuator. The foreign object may be positioned within a range of the jaws when the jaws are in an open configuration. A closing force may be applied to the opposing jaws with the self-actuating mechanism to secure the foreign object. The grasping device may then be withdrawn to retrieve the foreign object.

In one aspect, the self-actuating mechanism is biased so that the closing force is applied to the opposing jaws and the opposing jaws remain closed in a free-standing state when no force is imparted to the actuator.

In one aspect, applying the opening force with the actuator may involve applying a distal force to the actuator.

In one aspect, the opening force may be applied to the actuation wire by applying a force in the opposite direction to the actuator.

In one aspect, the closing force applied by the self-actuating mechanism may be augmented by applying force to the actuator.

In one aspect, the grasping device may be directly connected to a cystoscope or other imaging equipment or medical device using an adapter. The adapter may be telescopically adjusted to set a desired position of the grasping device relative to the cystoscope or other imaging equipment or medical device and the adapter may be locked in that position.

In one aspect, the foreign object may be located in the patient's prostatic urethra, urinary bladder, urinary tract or urinary system. The foreign object may be an implant.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. Moreover, as used in this specification and the appended claims, the singular forms "a," "an" and "the" include plural referents unless the content clearly dictates otherwise.

With respect to orientation of the various structures and anatomical references described herein, the term "proximal" and "distal" are relative to the perspective of the medical professional, such as a urologist, who is manipulating the delivery system of the disclosure to deploy the implants described herein. Accordingly, those features of the delivery system held by the hand of the urologist are at the "proximal" end and the assembled system and the implant, initially in its compressed configuration, is located at the "distal" end of the delivery system.

As noted above, the techniques of this disclosure feature a grasper having an auto-locking function. The handle includes a self-actuating mechanism to automatically apply a grasping force to the jaws at the distal end of the device, reducing or eliminating the need for the user to apply the constant forward pressure described above that is characteristic of the prior art graspers. Particularly, a grasper embodying features of this disclosure employ the self-actuating mechanism to close and maintain the distal jaw closure.

Figure 2:
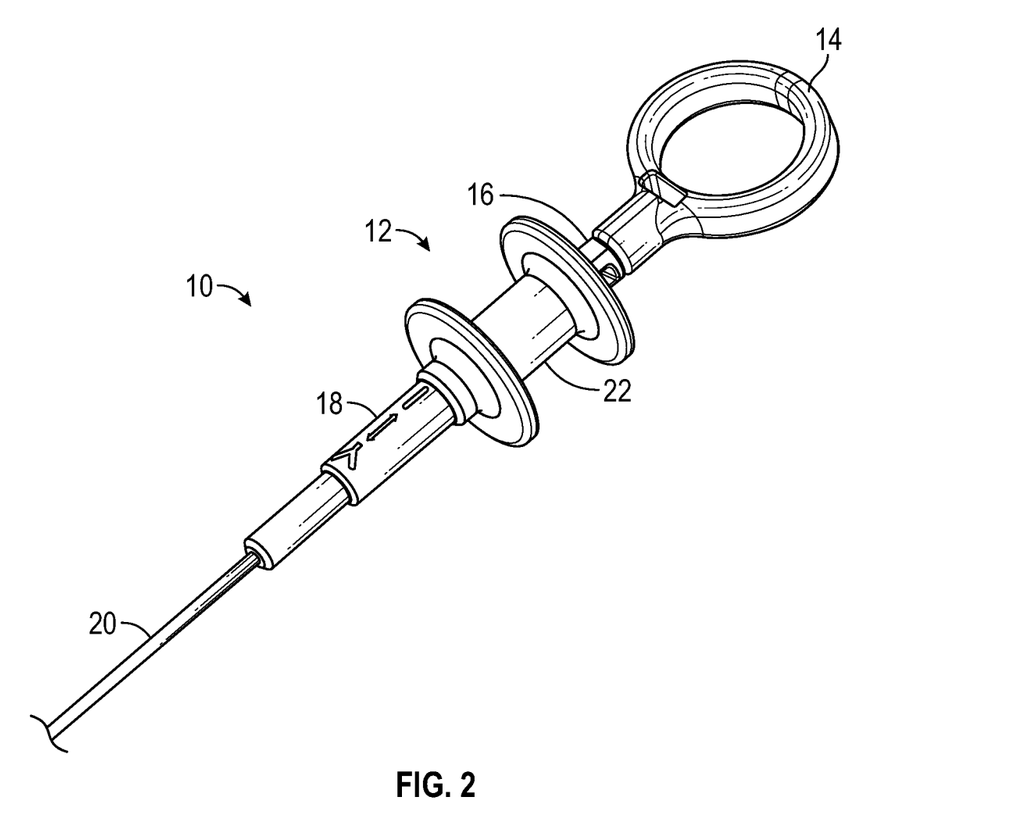
FIG. 2 schematically depicts an isometric view of a self-actuating grasper according to an embodiment.
Figure 3:
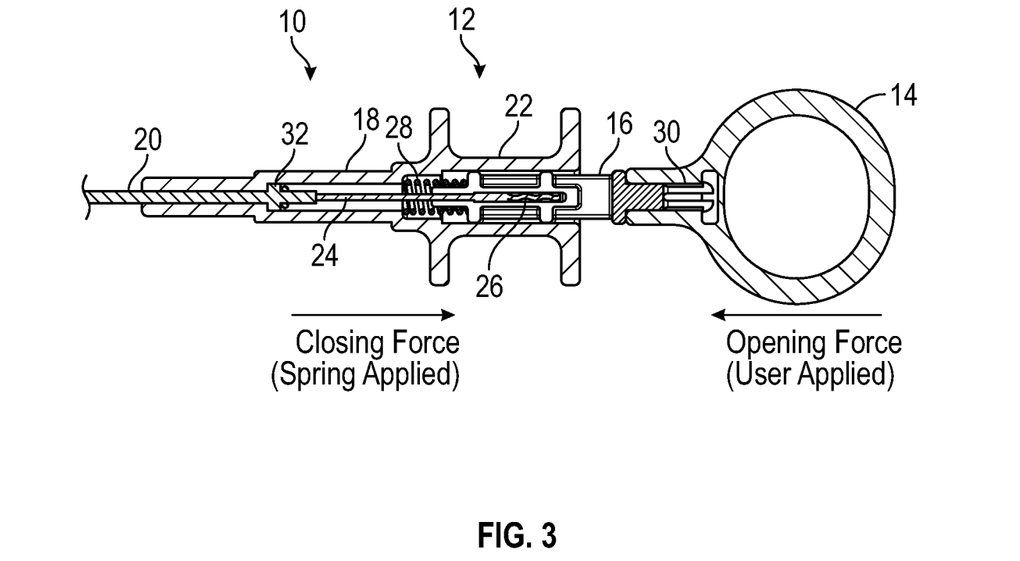
FIG. 3 schematically depicts a cross-sectional view of the self-actuating grasper according to an embodiment.
Figure 4:
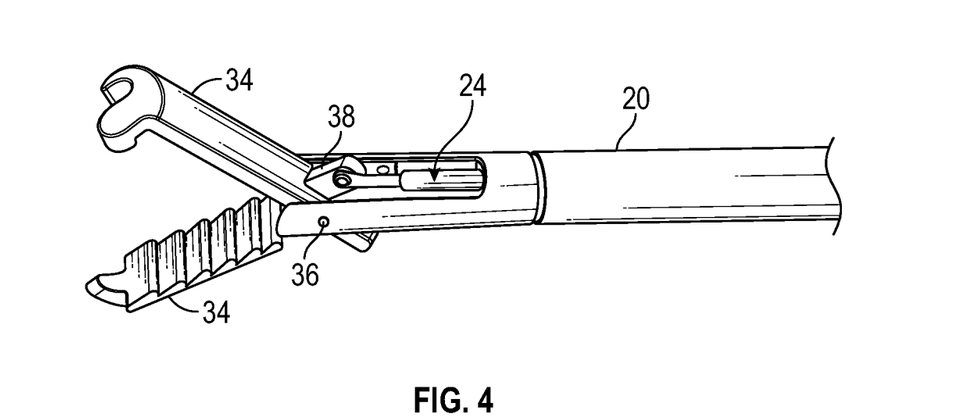
FIG. 4 schematically depicts a detail view of a distal end of the self-actuating grasper according to an embodiment.

To help illustrate aspects of this disclosure, the handle and self-actuating mechanism at the proximal end of an exemplary grasper is schematically depicted in isometric view in FIG. 2. As shown, the proximal end of grasper 10 has handle 12 that includes thumb loop 14 and plunger 16 extending coaxially into barrel 18. Thumb loop 14 is an actuatable element activated by the user and other embodiments can employ different configurations, such as a slider, a lever, a button or others as known in the art. Elongated shaft member 20 extends distally from handle 12. Flange 22 provides an element that can be gripped by the user and to aid in manipulation and use of grasper 10, particularly when engaging the thumb loop 14 or other actuator. Further, FIG. 3 schematically depicts handle 12 in cross-sectional view to show details of the self-actuating mechanism. Particularly, plunger 16 is coupled to actuation wire 24 at connection 26. In the depicted embodiment, this connection 26 is a friction fit but any suitable attachments can be used. Actuation wire 24 extends coaxially through shaft member 20 to the distal end of grasper 10 as described below. Handle 12 is configured to allow the user's thumb to be placed in thumb loop 14 and the user's fingers around flange 22. The self-actuation mechanism is driven by compression spring 28, one end of which is secured to the distal end of plunger 16 while the other is secured to barrel 18. Therefore, the self-actuation mechanism causes plunger 16 to transmit a withdrawal force to actuation wire 24. Conversely, depressing thumb loop 14 while holding flange 22 can overcome the withdrawal force imparted by spring 28. As desired, thumb loop 14 can be secured to plunger 16 by a snap-fit connection 30, allowing for partial disassembly and/or reassembly of handle 12 to facilitate packaging, sterilization or other purpose. Alternatively, any other suitable means of attachment can be used, including permanent attachment, or thumb loop 14 and plunger 16 can be a unitary structure. The proximal end 32 of shaft member 20 may include a feature, such as a flange, to help secure and position shaft member 20 with respect to barrel 18. Turning now to FIG. 4, a detail view of the distal end of grasper 10 is shown, where opposing jaws 34 are connected at an intermediate location by scissor pivot 36 and can transition between open and closed configurations. Actuation wire 24 is coupled to the proximal ends 38 of jaws 34, so that the withdrawal force is a closing force and causes jaws 34 to pivot to a closed position when applied to actuation wire 24, while application of a distal force is an opening force and pivots jaws 34 to the open position shown when applied to actuation wire 24. As will be appreciated, the force of spring 28 is directly related to the clamping force of jaws 34. As desired, the user can selectively augment the closing pressure by manually depressing thumb loop 14 while holding flange 22. It should also be appreciated that this design can be adapted to employ jaws 34 that are driven closed by a distal force as opposed to a withdrawal force by substituting an extension spring 28 for the compression spring 28. With this modification, the spring 28 still automatically supplies the closing force and the user can apply the opening force by withdrawing thumb loop 14.

Figure 5:
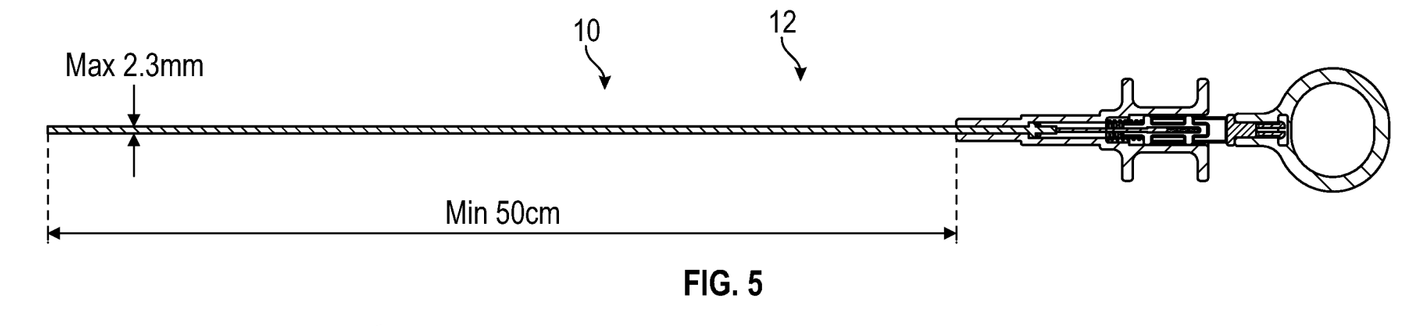
FIG. 5 schematically depicts an overview of the self-actuating grasper showing exemplary dimensions according to an embodiment.

Shaft member 20 is desirably thin, flexible, soft, and yet strong enough to facilitate advancement without kinking while also offering sufficient columnar strength to transmit forces through actuation wire 24. In one embodiment, shaft member 20 is formed from a reinforced polymer extrusion. For example, the polymer extrusion may be made with materials such as PEBA (Polyether Block Amide), Polytetrafluoroethylene (PTFE), etc. The extrusion may also be a multilayer construction using different polymers or the same polymer but with differing hardness. The reinforcement may be metallic, such as stainless steel, nitinol, etc., or a polymer, such as PEEK (Poly-Ether-Ether-Ketone), Nylon, etc. The reinforcement may be arranged in a coil or braided pattern and may not necessarily extend across the entire length of the shaft member 20. Alternatively, shaft member 20 may be constructed from extruded polymers alone. Shaft member 20 can also have a liner along its inner diameter to reduce friction with actuation wire 24, which may be made of PTFE, Nylon, or other materials with low coefficients of friction. Shaft member 20 may also be coated with additional lubricious or hydrophilic material on its outer diameter to help facilitate advancement through the urinary tract or other location in the body. Suitable wall thicknesses for shaft member 20 are 0.001-0.025", or more preferably 0.003-0.015". In one embodiment, suitable dimensions of grasper 10 may be as indicated in FIG. 5, although it will be recognized that these dimensions can be modified as desired to suit the intended application.

In light of the above disclosure, it will be appreciated that during one illustrative example operating grasper 10, the user manipulates handle 12 to advance shaft member 20 to a desired location within the patient's body, such as by positioning jaws 34 proximally adjacent to the foreign object, for example, an implant located in urethra, to be removed. The user may then depress thumb loop 14 while holding flange 22 to overcome the bias of spring 28 and open jaws 34. Further advancement of shaft member 20 can then position the foreign object within the range of jaws 34. Next, releasing the pressure on thumb loop 14 allows spring 28 to attempt to return to its native length, imparting the withdrawal force to actuation wire 24 and correspondingly causing jaws 34 to pivot towards the closed position to grasp the foreign object. The self-actuation mechanism described above maintains the force or pressure and holds the grasper 10 in the closed position until the force pressure is released by the user by again withdrawing thumb loop 14. This design minimizes the need for constant pressure to be applied with actuation methods used on currently available graspers and reduces user hand fatigue. As will be appreciated, the self-actuation mechanism is not limited to just a spring-driven design. A cam mechanism or similar mechanisms may also be employed by those skilled in the art to achieve similar results. The self-actuating grasper 10 described is capable of achieving grasping or grip forces, approximately normal to the jaws 34, between 1-20 Newtons or more preferably between 1-5 Newtons, depending on the mechanism, jaw geometry, and spring constant of compression spring 28. Once the prostatic implant, prostatic tissue expander or foreign object is gripped, the self-actuating grasper 10 is capable of withstanding retrieval forces, applied longitudinally along the axis of the shaft member 20, between 5-50 Newtons or more preferably between 5-20 Newtons.

Figure 6:
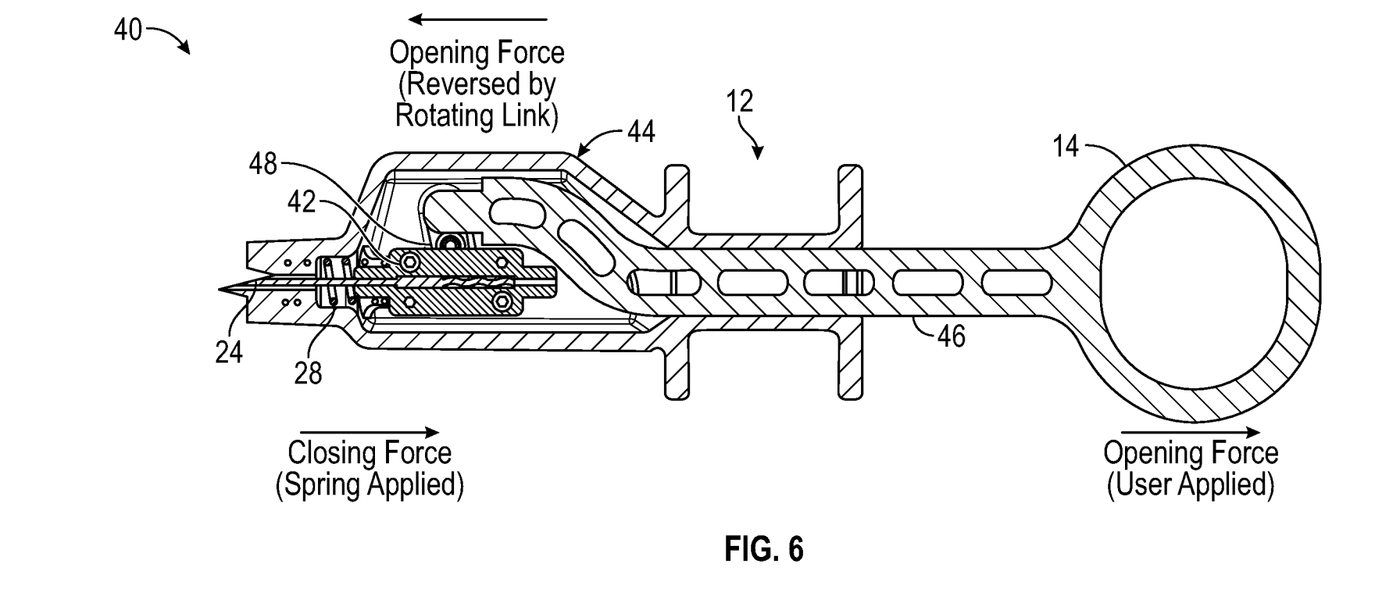
FIG. 6 schematically depicts a detail view of the handle end of another self-actuating grasper according to an embodiment.

In another embodiment, grasper 40 is schematically depicted in FIG. 6, with similar elements employing the same reference numbers. In this embodiment, the self-actuating mechanism is configured so that the user applies a withdrawal force to open the jaws 34. Here, plunger 42 is coupled to actuation wire 24 and contained wholly within body 44 of handle 12. Similar to the previous embodiment, plunger 42 is biased in a proximal direction by spring 28, thereby providing the closing force to jaws 34 (not shown in this view). To reverse the direction of force applied by the user, plunger 42 is coupled to extension 46 of thumb loop 14 by rotating link 48. As such, the user applies a withdrawal force to thumb loop 14 as the opening force. By changing gear sizes in rotating link 48, different leverage ratios can be obtained for the force applied to thumb loop 14. As with the previous embodiment, the user can augment the closing force by manually withdrawing thumb loop 14 given that the direction of user applied force is reversed in this configuration. Also, a modification of this embodiment similar to the previous embodiment can be achieved by substituting an extension spring for the compression spring. Once more, the spring automatically supplies the closing force while the user can apply the opening force by depressing thumb loop 14.

Figure 7:
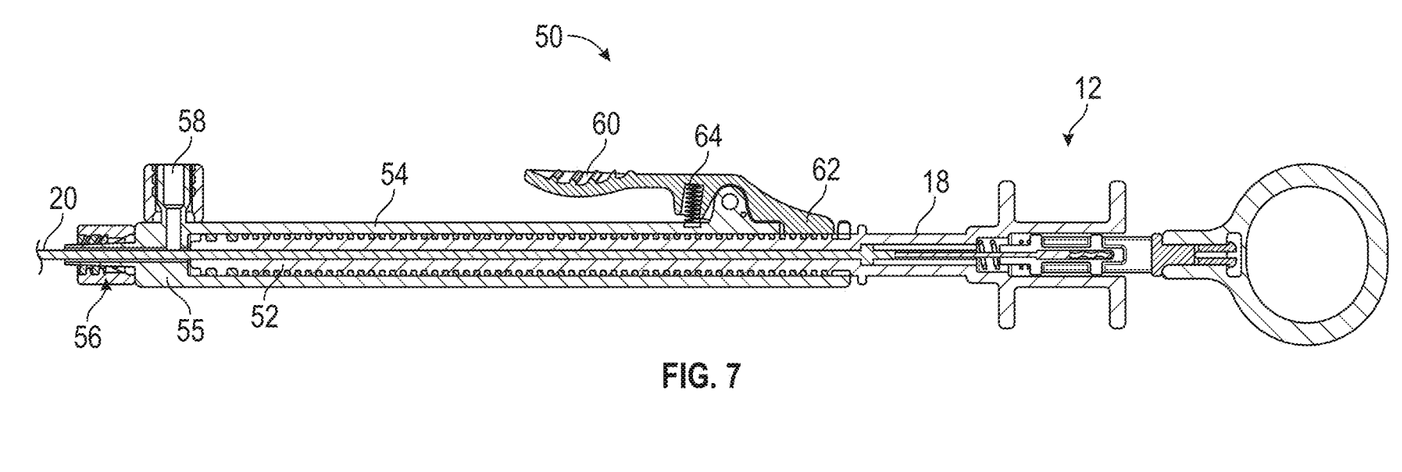
FIG. 7 schematically depicts a proximal portion of another self-actuating grasper that directly connects to a cystoscope according to an embodiment.

In yet another embodiment, grasper 50 is schematically depicted in FIG. 7 and incorporates an adapter for directly connecting to a cystoscope. Handle 12 can incorporate any of the self-actuating mechanisms discussed above, although the first embodiment is shown. Extension 52 of barrel 18 is coaxially disposed within body 54 of cystoscope adapter 55 in a telescoping arrangement. As before, shaft member 20 extends from barrel 18 and coaxially through extension 52. Body 54 of adapter 55 features Luer lock ring 56 at its distal end for connection to a cystoscope and an irrigation line may be coupled to grasper 50 though irrigation connection 58. The telescoping arrangement of extension 52 of barrel 18 and body 54 of adapter 55 allows the relative positioning of grasper 50 to the cystoscope to be adjusted to accommodate different designs. Once the appropriate position within the cystoscope is achieved, grasper 50 can be fixed relative to the cystoscope. Notably, the embodiment shown here features rack-like teeth 62 along the outer diameter of extension 52. Lock lever 60 is pivotally connected to body 54, with corresponding rack-like teeth 62 that are biased into engagement with the teeth on extension 52 by compression spring 64. When the user depresses lock lever 60, the length of extension 52 of barrel 18 disposed within body 54 of adapter 55 can be telescopically adjusted and when lock lever 60 is released, spring 64 causes the lever 60 to pivot and engage teeth 62 with those on extension 52 to fix the relative position of grasper 50 and the cystoscope. Other suitable techniques may be employed to lock extension 52 at a desired degree of extension 52 within body 54, such as a frictional collet or clamp, a depressible projection that engages one of a plurality of longitudinally distributed holes along the body 54, or other methods known to those in the art.

Figure 8:
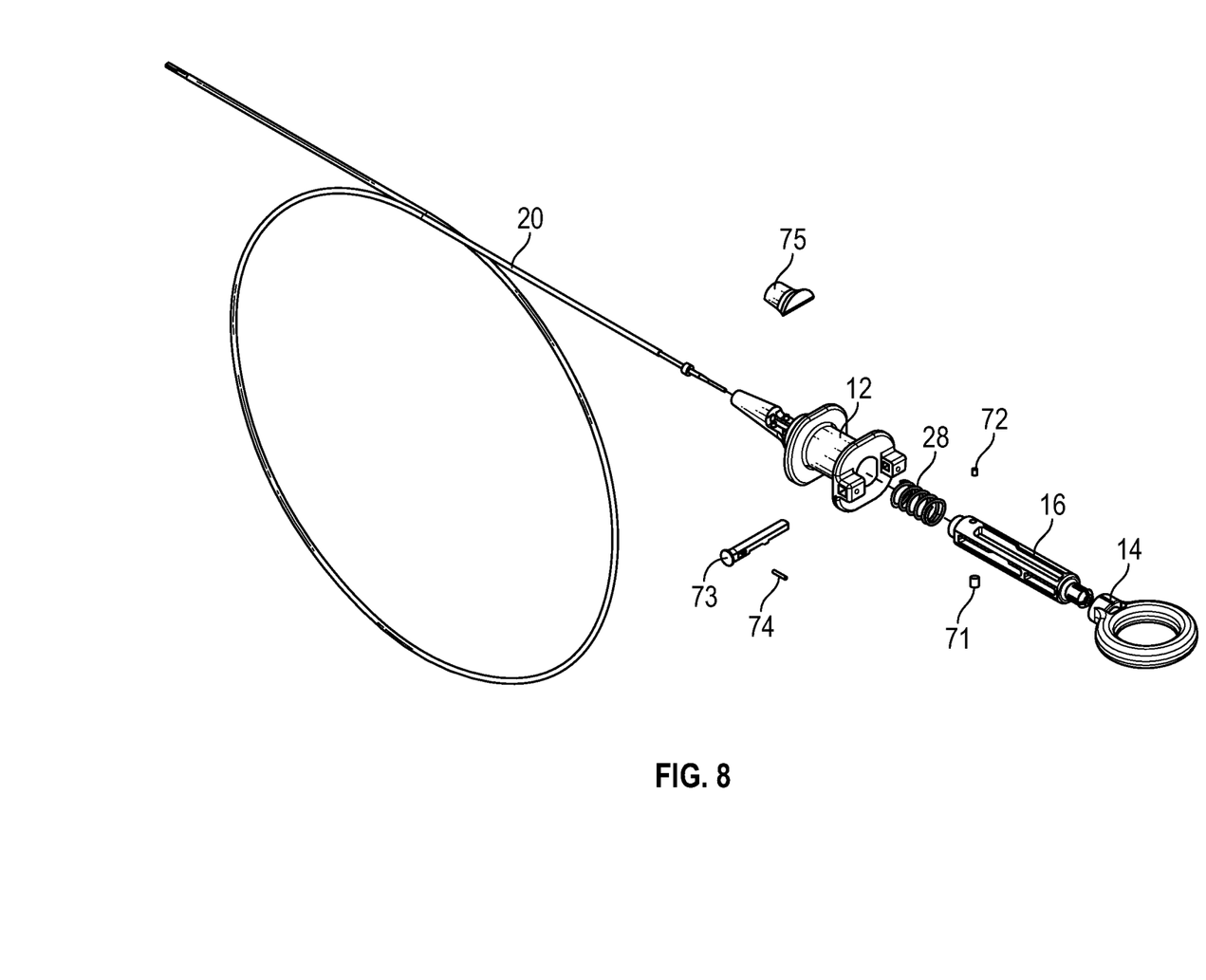
FIG. 8 schematically depicts an exploded detail view of the self-actuating grasper according to an embodiment.

In yet another embodiment, the handle 12 and self-actuating mechanism at the proximal end of an exemplary grasper 10 incorporate a safety feature to prevent damage to the distal jaws 34 assembly during transit and storage. As in FIGS. 2-4, it comprises thumb loop 14 connected to plunger 16, shaft member 20 and activated by the compression spring 28. Referring to FIG. 8, these components are assembled and held in place by a threaded insert 71, a set screw 72, a release pin 73, a spring pin 74 and a cowling (or cover) 75. The release pin 73 locks compression spring 28 in the compressed state and protects the grasper 10 in the packaged configuration during transit and storage, prior to use. Locking the spring 28 prevents damage to the small pin joints between the jaws 34 at the distal end of the shaft member 20, shown in FIG. 9. Before use, the user presses the release pin 73 and the compression spring 28 is free to apply force on the shaft member 20, which then activates the proximal movement of thumb loop 14 towards the user and closes the grasper jaws 34. To use the grasper, the user squeezes the thumb loop 14 distally, which compresses the compression spring 28, shortening the distance between the handle 12 and thumb loop 14, and opening the jaws 34.

Figure 9A:
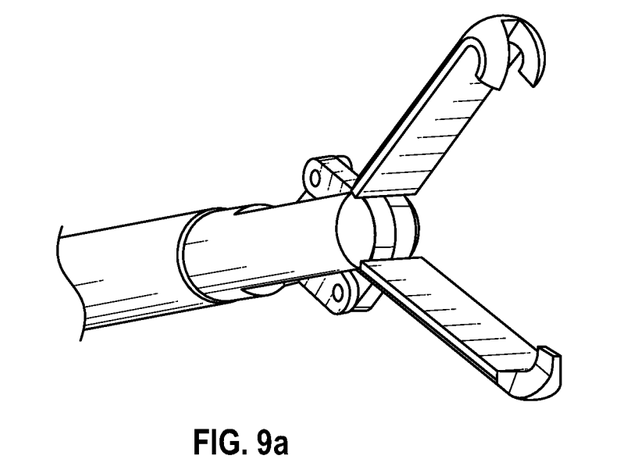
FIG. 9a-9c schematically depicts a detail view of a distal end of the self-actuating grasper according to an embodiment in open and closed configurations.
Figure 9B:
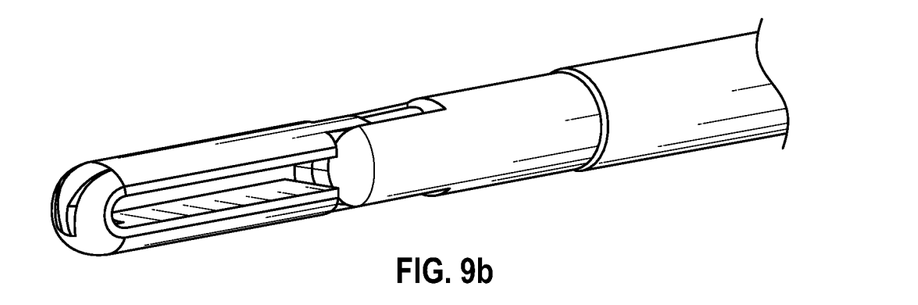
Figure 9C:
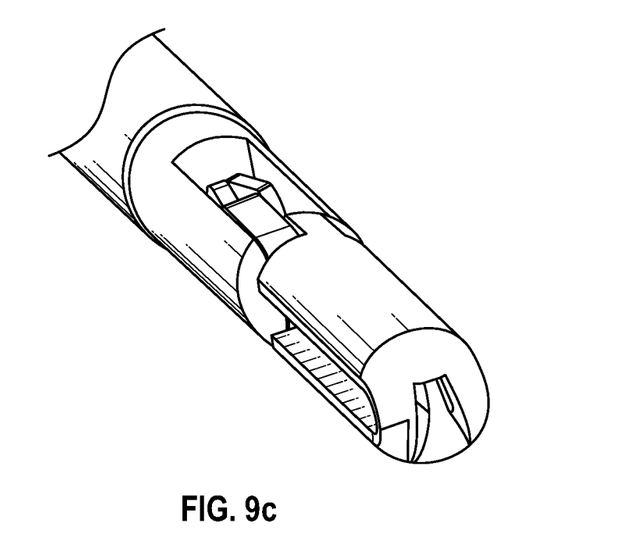

FIG. 9 shows the detailed view of the distal end of another embodiment of the self-actuating grasper 10 in the fully open (as shown in FIG. 9a) and fully closed conditions (as shown in FIGS. 9b and 9c). In this embodiment, the opposing jaws 34 can be smooth without serrated teeth. The absence of serrations on inner surfaces of the jaws 34 provides greater gap between opposing jaws 34 and can assist securing and retrieval of an expander implant, stent, or a foreign object. The jaws 34 are also designed with features on the ends to interlock and secure the expander, implant or other foreign object. The end of one jaw 34 has a projection in the middle and the opposing jaw 34 has a groove that interlocks or with the projection. Note that in the closed state, there is some gap or opening between the interlocked jaws 34 in the fully closed condition. The gap between the jaws 34 enhances the ability of the grasper 10 to securely grab and snare or retrieve the expander, implant or any other foreign object from the body.

As will be appreciated from the above discussion and figures, the self-actuating grasper design of the present disclosure can be used to assist the retrieval of a foreign object, including a stent, an expander or other implant, or a naturally occurring deposit such as a stone or calculi, from the prostatic urethra, urinary bladder, ureters, kidneys urinary tract or urinary system in addition to other suitable applications. By employing the techniques of this disclosure, such a grasper may exhibit a number of beneficial characteristics, including without limitation: 1) the ability to securely grip the foreign object to facilitate retrieval; 2) being atraumatic to urethra and other anatomical structures during retrieval of foreign object; 3) being compatible with commonly used flexible and rigid cystoscopes, other medical imaging equipment and ancillary medical devices used in medical procedures; 4) allowing for self-actuation to automatically lock, together with the ability to un-lock as desired; 5) the ability to rotate axially, such as by having adequate torque transmission, to position for engagement with foreign object for retrieval; 6) allowing continuous imaging, with irrigation through the working channel of the cystoscope as needed, during the retrieval procedure; and 7) having sufficient locking force to firmly hold the foreign object, without loss, during the retrieval procedure.

The exemplary embodiments disclosed above are merely intended to illustrate the various utilities of this disclosure. It is understood that numerous modifications, variations and combinations of functional elements and features of the present disclosure are possible in light of the above teachings and, therefore, within the scope of the appended claims, the present disclosure may be practiced otherwise than as particularly disclosed and the principles of this disclosure can be extended easily with appropriate modifications to other applications.

All patents and publications are herein incorporated for reference to the same extent as if each individual publication was specifically and individually indicated to be incorporated by reference. It should be understood that although the present disclosure has been specifically disclosed by preferred embodiments and optional features, modification and variation of the concepts herein disclosed may be resorted by those skilled in the art, and that such modifications and variations are considered to be within the scope of this disclosure.

What is claimed is:

1. A grasping device, comprising:
   a handle;
   an actuator on the handle coupled to an actuator wire;
   an elongated shaft member extending distally from the handle with the actuator wire coaxially and longitudinally disposed therein;
   a plunger extending coaxially within a barrel of the handle, the plunger being coupled to the actuator wire; and
   opposing jaws pivotally attached to a distal end of the elongated shaft member that are coupled to the actuator wire, the opposing jaws configured to pivot between an open configuration and a closed configuration in response to proximal and distal longitudinal movement of the actuator wire inside the elongated shaft member, wherein the plunger when in a proximal position by a spring that causes the actuator wire to be pulled proximally and longitudinally to impart a closing force to the opposing jaws through the actuator wire sufficient to maintain the opposing jaws in the closed configuration and wherein actuation of the actuator is configured to cause the plunger to move to a distal position, which causes the actuator wire to move distally and longitudinally to impart an opening force to the opposing jaws through the actuator wire sufficient to overcome the closing force imparted by the spring and pivot the opposing jaws to the open configuration.

2. The grasping device of claim 1, wherein the spring is a compression spring such that the plunger is biased in a proximal direction and the closing force is a withdrawal force applied to the actuator wire.

3. The grasping device of claim 2, wherein the actuator is configured to impart the opening force in a distal direction when the user applies a distal force to the actuator.

4. The grasping device of claim 2, wherein the actuator is configured to impart the opening force in a distal direction when the user applies a withdrawal force to the actuator.

5. The grasping device of claim 1, wherein an extension of the actuator is coupled to the plunger by a rotating link that reverses the direction of force applied through the actuator.

6. The grasping device of claim 1, wherein the actuator is configured to augment the closing force when force is applied to the actuator in a direction opposite of that associated with the opening force.

7. The grasping device of claim 1, wherein the spring is an extension spring such that the plunger is biased in a distal direction and the closing force is a distal force applied to the actuation wire.

8. The grasping device of claim 7, wherein the actuator is configured to impart the opening force in a withdrawal direction.

9. The grasping device of claim 1, further comprising an adapter configured to provide direct connection to a cystoscope.

10. The grasping device of claim 9, further comprising a barrel extension telescopically disposed within a body of the adapter allowing a position of the grasping device relative to the cystoscope to be adjusted.

11. The grasping device of claim 10, wherein the barrel extension is configured to be locked in an adjusted position.

12. The grasping device of claim 9, wherein the adapter further comprises an irrigation port.

13. A method for retrieving a foreign object from a location in a patient's body, comprising:
    providing a grasping device having a handle with a self-actuating mechanism, an actuator on the handle coupled to an actuator wire, an elongated shaft member extending distally from the handle with the actuator wire coaxially and longitudinally disposed therein, a plunger extending coaxially within a barrel of the handle, the plunger being coupled to the actuator wire, and opposing jaws pivotally attached to at a distal end of the elongated shaft member that are coupled to the actuator wire, the opposing jaws configured to pivot between an open configuration and a closed configuration in response to proximal and distal longitudinal movement of the actuator wire inside the elongated shaft member, wherein the plunger when in a proximal position by a spring that causes the actuator wire to be pulled proximally and longitudinally to impart a closing force to the opposing jaws through the actuator wire sufficient to maintain the opposing jaws in the closed configuration and wherein actuation of the actuator is configured to cause the plunger to move to a distal position, which causes the actuator wire to move distally and longitudinally to impart an opening force to the opposing jaws through the actuator wire sufficient to overcome the closing force imparted by the spring and pivot the opposing jaws to the open configuration;
    advancing the grasping device through a lumen of a medical device until the opposing jaws are adjacent to the foreign object;
    applying the opening force through the actuator wire to the opposing jaws with the actuator;
    positioning the foreign object within a range of the opposing jaws when the opposing jaws are in the open configuration;
    applying the closing force to the opposing jaws with the self-actuating mechanism to secure the foreign object; and
    withdrawing the grasping device and retrieving the foreign object.

14. The method of claim 13, wherein the opposing jaws remain closed in a free-standing state when no force is imparted to the actuator.

15. The method of claim 13, wherein applying the opening force with the actuator comprises applying a distal force to the actuator.

16. The method of claim 13, wherein the opening force is applied to the actuator wire by applying a force in the opposite direction to the actuator.

17. The method of claim 13, further comprising augmenting the closing force applied by the self-actuating mechanism by applying a force to the actuator.

18. The method of claim 13, further comprising directly connecting the grasping device to a cystoscope or other imaging equipment or medical device using an adapter.

19. The method of claim 18, further comprising telescopically adjusting the adapter to set a desired position of the grasping device relative to the cystoscope or other imaging equipment or medical device and locking the adapter.

20. The method of claim 13, wherein the foreign object is located in the patient's prostatic urethra, urinary bladder, urinary tract or urinary system.

21. The method of claim 20, wherein the foreign object is an implant.

* * * * *